United States Patent

Eller et al.

[11] Patent Number: 5,840,988
[45] Date of Patent: Nov. 24, 1998

[54] PREPARATION OF AMINES FROM OLEFINS ON ZEOLITES OF THE MCM-49 OR MCM-56 TYPE

[75] Inventors: Karsten Eller, Ludwigshafen; Rudolf Kummer, Frankenthal, both of Germany

[73] Assignee: BASF Aktiengesellschaft, Ludwigshafen, Germany

[21] Appl. No.: 977,893

[22] Filed: Nov. 25, 1997

[30] Foreign Application Priority Data

Dec. 3, 1996 [DE] Germany ............... 196 49 944.5

[51] Int. Cl.$^6$ ................................................. C07C 209/02
[52] U.S. Cl. ............................................................. 564/485
[58] Field of Search ............................................. 564/485

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |
| 4,929,758 | 5/1990 | Taglieber et al. | 564/485 |
| 5,362,697 | 11/1994 | Fung et al. | 502/71 |
| 5,371,310 | 12/1994 | Bennett et al. | 585/467 |
| 5,453,554 | 9/1995 | Cheng et al. | 585/467 |

FOREIGN PATENT DOCUMENTS

| | | |
|---|---|---|
| 2092964 | 3/1993 | Canada . |
| 101 921 | 3/1984 | European Pat. Off. . |
| 132 736 | 2/1985 | European Pat. Off. . |
| 133 938 | 3/1985 | European Pat. Off. . |
| 305 564 | 3/1989 | European Pat. Off. . |
| 431 451 | 6/1991 | European Pat. Off. . |
| 587424 | 3/1994 | European Pat. Off. . |
| 590 078 | 4/1994 | European Pat. Off. . |
| 754676 | 7/1996 | European Pat. Off. . |
| 802176 | 4/1997 | European Pat. Off. . |
| 42 06 992 | 3/1992 | Germany . |
| 19526502 | 7/1995 | Germany . |

OTHER PUBLICATIONS

Brunet et al., *J. Mol. Catal.*, 49, 1989, pp. 235–259.
*J. Phys. Chem.*, 100, 1996, pp. 3788–3798.
Corma et al., *Stud. Surf. Sci. Catal.*, 37, 1987, pp. 495–503.

*Primary Examiner*—Brian M. Burn
*Attorney, Agent, or Firm*—Keil & Weinkauf

[57] ABSTRACT

A process for preparing amines of the formula I $$R^5\!\!-\!\!\underset{R^6}{\overset{}{\text{CH}}}\!\!-\!\!\underset{R^4}{\overset{R^3}{\text{C}}}\!\!-\!\!\underset{}{\overset{R^1}{\text{N}}}\!\!-\!\!R^2 \quad (I)$$

where $R^1, R^2, R^3, R^4, R^5, R^6$ are hydrogen, $C_1$- to $C_{20}$-alkyl, $C_2$- to $C_{20}$-alkenyl, $C_2$- to $C_{20}$-alkynyl, $C_3$- to $C_{20}$-cycloalknyl, $C_4$- to $C_{20}$-alkyl-cycloalkyl, $C_4$- to $C_{20}$-cycloalkyl-alkyl, aryl, $C_7$- to $C_{20}$-alkylaryl or $C_7$- to $C_{20}$-aralkyl, $R^1$ and $R^2$ jointly are a saturated or unsaturated $C_3$- to $C_9$-alkylene divalent chain and $R^3$ or $R^5$ are $C_{21}$- to $C_{200}$-alkyl, $C_{21}$- to $C_{200}$-alkenyl or jointly are a $C_2$- to $C_{12}$-alkylene divalent chain, by reacting olefins of the formula II $$\underset{R^6}{\overset{R^5}{\phantom{x}}}\!\!\!C\!=\!C\!\!\!\underset{R^4}{\overset{R^3}{\phantom{x}}} \quad (II)$$

where $R^3$, $R^4$, $R^5$ and $R^6$ have the abovementioned meanings, with ammonia or primary or secondary amines of the formula III $$H\!-\!N\!\!\!\underset{R^2}{\overset{R^1}{\phantom{x}}} \quad (III)$$

where $R^1$ and $R^2$ have abovementioned meanings, at from 200° to 350° C. and from 100 to 300 bar in the presence of a heterogeneous catalyst, by using zeolites of the MCM-49 or MCM-56 type as the heterogeneous catalyst.

12 Claims, No Drawings

PREPARATION OF AMINES FROM OLEFINS ON ZEOLITES OF THE MCM-49 OR MCM-56 TYPE

Preparation of amines from olefins on zeolites of the MCM-49 or MCM-56 type

The present invention describes a process for preparing amines by reacting ammonia or primary or secondary amines with olefins at elevated temperatures and pressures in the presence of zeolites of the MCM-49 or MCM-56 type.

An overview of the methods for aminating olefins is provided in "Functionalization of Alkenes: Catalytic Amination of Monoolefins", J. J. Brunet et al., J. Mol. Catal., 49 (1989), pp. 235 to 259.

In principle there are two catalytic mechanisms. The olefin is coordinated via a metal complex. This activated species can be attacked by the nucleophilic amine and form a more highly aminated product. The amine can be chemisorbed on acid sites or on metal sites (via metal amides) and thus activated be reacted with the olefin.

Among highly suitable catalysts are zeolites. They are distinguished by their high number of catalytically active sites in conjunction with a large surface area. The zeolites described differ with respect to type and aftertreatment (eg. thermal treatment, dealumination, acid treatment, metal ion exchange, etc.). Relevant examples can be found in U.S. Pat. No. 4,375,002, U.S. Pat. No. 4 536 602, EP-A-305 564, EP-A-101 921, DE-A-42 06 992.

EP-A-133 938, EP-A-431 451 and EP-A-132 736 describe processes in which boron zeolites, gallium zeolites, aluminozeolites and iron silicate zeolites are used for preparing amines from olefins and where the possibility of doping these zeolites with alkali metals, alkaline earth metals and transition metals is noted.

CA-A-2 092 964 discloses a process for preparing amines from olefins, which employs BETA zeolites, which are defined as crystalline aluminosilicates of a specific composition having a pore size of more than 5 Å. Preference is given to the use of metal- or halogen-modified beta-zeolites.

All processes for synthesizing amines from olefins on these-catalysts are distinguished by a low amine yield or low space-time yield or result in rapid deactivation of the catalysts.

It is therefore an object of the present invention to overcome these drawbacks.

We have found that this object is achieved by a novel and improved process for preparing amines of the formula I

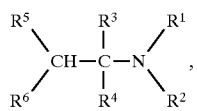  (I)

where $R^1, R^2, R^3, R^4, R^5, R^6$ are hydrogen, $C_1$- to $C_{20}$-alkyl, $C_2$- to $C_{20}$-alkenyl, $C_2$- to $C_{20}$-alkynyl, $C_3$- to $C_{20}$-cycloalkyl, $C_4$- to $C_{20}$-alkyl-cycloalkyl, $C_4$- to $C_{20}$-cycloalkyl-alkyl, aryl, $C_7$- to $C_{20}$-alkylaryl or $C_7$- to $C_{20}$-aralkyl, $R^1$ and $R^2$ jointly are a saturated or unsaturated $C_3$- to $C_9$-alkylene divalent chain and $R^3$ or $R^5$ are $C_{21}$- to $C_{200}$-alkyl, $C_{21}$- to $C_{200}$-alkenyl or jointly are a $C_2$- to $C_{12}$-alkylene divalent chain, by reacting olefins of the formula II

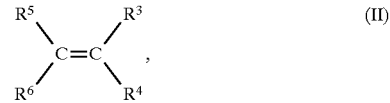  (II)

where $R^3$, $R^4$, $R^5$ and $R^6$ have the abovementioned meanings, with ammonia or primary or secondary amines of the formula III

  (III)

where $R^1$ and $R^2$ have the abovementioned meanings, at from 200° to 350° C. and from 100 to 300 bar in the presence of a heterogeneous catalyst, wherein the heterogeneous catalyst used comprises zeolites of the MCM-49 or MCM-56 type.

The novel process can be carried out as follows:

The olefin II and ammonia or the primary or secondary amine III can be reacted at from 200° to 350° C., preferably from 220° to 333° C., particularly preferably from 230° to 320° C. and at from 100 to 300 bar, preferably from 120 to 300 bar, particularly preferably from 140 to 290 bar in the presence of zeolites of the MCM-49 or MCM-56 type as a catalyst, eg. in a pressurized reactor, and the amine obtained can be preferentially separated off and the unreacted starting materials be recycled.

The present process is distinguished by a very good yield at high selectivity and high space-time yield. Moreover, the deactivation of the catalyst has been repressed.

The novel process is distinguished by the fact that a small excess of ammonia or amine is sufficient to achieve a high selectivity for the desired reaction product and to avoid the dimerization and/or oligomerization of the olefin employed.

One embodiment of this process comprises ammonia and/or amines III being passed, together with the olefin II, mixed in a molar ratio of from 1:1 to 5:1, to a fixed-bed reactor and being reacted at from 100 to 300 bar and at from 200° to 350° C. in the gas phase or in the supercritical state.

From the reaction output the desired product can be obtained with the aid of known methods, for example distillation or extraction and can, if required, be brought to the desired purity by means of further separation operations. The unreacted starting materials are preferably, as a rule, recycled into the reactor.

The starting materials used can be singly or multiply unsaturated olefins II, in particular those having from 2 to 10 C atoms or mixtures thereof, and polyolefins. Owing to the less pronounced tendency to polymerize, monoolefins are more suitable than di- and polyolefins, although the latter can likewise be reacted selectively with the aid of larger excesses of ammonia or amine. The position of the equilibrium and consequently the conversion ratio to the desired amine depends very markedly on the reaction pressure chosen. A high pressure favors the addition product, although generally, on technical and economic grounds, the pressure range up to 300 bar represents the optimum. The selectivity of the reaction is influenced not only by variables such as the excess of ammonia/amine and the catalyst, but also, largely, by the temperature. While the reaction rate of the addition reaction does increase markedly as the temperature rises, competing cracking and recombination reactions of the olefin are promoted at the same time. Moreover, an increase in temperature is not beneficial, from the thermodynamic point of view. The position of the temperature optimum in terms of conversion ratio and selectivity depends on the constitution of the olefin, of the amine used and of the catalyst and is usually in the range of from 200° to 3500° C.

Suitable catalysts for the amination of olefins are zeolites of the MCM-49 or MCM-56 type. MCM-49 is disclosed, for example, by EP-A-590 078, and MCM-56 is disclosed by U.S. Pat. No. 5 362 697.

MCM-49 is a three-dimensional zeolite which to a certain extent is related to the two-dimensional MCM-22 zeolite which is disclosed by the older German Application DE-A-195 26 502 for the amination of olefins. The differentiating features of the X-ray powder diffractograms are described in J. Phys. Chem. 100 (1996), 3788 to 3798, by Lawton et al. MCM-56 likewise forms part of the same zeolite family, as described in more detail in U.S. Pat. No. 5,362,697 and U.S. Pat. No. 5,453,554. The synthesis of all three zeolites uses hexamethylene imine as the template (structure-forming agent), and their close relationship is thus understandable. For the purpose of the present application, zeolites according to the invention of the MCM-49 or MCM-56 type subsume not only the pure zeolites of this type but also mixtures thereof and mixtures of MCM-49 and/or MCM-56 with MCM-22. Mixtures thereof subsume not only physical mixtures, but also mixed crystals of the three zeolites MCM-22, MCM-49 and MCM-56.

In addition to the zeolites of the MCM-49 or MCM-56 type, containing aluminum as the trivalent element in the $SiO_2$ matrix, other elements are furthermore possible for the purpose of the present application if their incorporation creates acidic sites. This is the case, for example, with boron zeolites, iron zeolites or gallium zeolites. The molar ratio of $SiO_2$ to the oxides of the trivalent elements, the so-called modulus $SiO_2 /M_2 O_3$ (M=Al, B, Ga, Fe), may vary, depending on the class of zeolite, between virtually infinite and a few tens. [B]-MCM-49 is described eg. in Lawton et al., J. Phys. Chem. 100 (1996) 3788 to 3798.

Instead of the trivalent element it is also possible for silicon to be substituted isomorphously by other quadrivalent elements, for example by Ge, Ti or Sn.

In addition to the classic zeolites based on $SiO_2$ it is also possible for analogous structures to be implemented on the basis of aluminum phosphates, referred to as AlPOs. If these contain aluminum and phosphorus in a ratio of greater than 1, they are likewise acidic and can be used for the purpose of the invention. If part of the phosphorus and/or simultaneously aluminum and phosphorus is replaced by silicon, this yields the materials referred to as SAPOs, which are likewise acidic. If in addition to aluminum and phosphorus various metal ions such as, for example, Li, B, Be, Mg, Ti, Mn, Fe, Co, Zn, Ga, Ge, As are also present, the term used is MeAPOs or, if silicon is also present, MeAPSOs, in which the negative charge of the $Me_aAl_bP_cSi_dO_e$ framework in each case is compensated for by cations. All such molecular sieves of the MCM-49 or MCM-56 type are subsumed under the catalysts according to the invention.

The zeolites of the MCM-49 or MCM-56 type according to the invention can be molded as such or alternatively with a binder in a ratio of from 98:2 to 40:60 wt % to produce extrudates or pellets. Suitable binders include various aluminum oxides, preferably boehmite, amorphous aluminosilicates with an $SiO_2/Al_2O_3$ ratio of from 25:75 to 95:5, silicon dioxide, preferably highly disperse $SiO_2$, mixtures of highly disperse $SiO_2$ and highly disperse $Al_2O_3$, highly disperse $TiO_2$ and clays. After molding, the extrudates or compacts are expediently dried at 110° C./16 hours and calcined at from 200° to 500° C./from 2 to 16 hours, which calcination tion can also take place directly in the amination reactor.

To increase the selectivity, the on-stream time and the number of possible regenerations it is possible to subject the novel zeolite catalysts of the MCM-49 or MCM-56 type to various modifications.

One modification of the catalysts consists in the option of the zeolites, molded or not molded, being subjected to ion exchange or doped with alkali metals such as Na and K, alkaline earth metals such as Ca, Mg, earth metals such as Tl, transition metals such as eg. Ti, Zr, Mn, Fe, Mo, Cu, Zn, Cr, noble metals and/or rare earth metals such as eg. La, Ce or Y.

An advantageous embodiment comprises the molded zeolites of the MCM-49 or MCM-56 type according to the invention being introduced into a flow tube and having eg. a halide, an acetate, an oxalate, a citrate or a nitrate of the above-described metals in dissolved form passed over them at from 20° to 100° C. An ion exchange of this type can be carried out eg. on the hydrogen form, ammonium form, alkali metal form of the zeolites of the MCM-49 or MCM-56 type according to the invention.

A further option of applying metal to the zeolites of the MCM-49 or MCM-56 type according to the invention consists in the material being impregnated eg. with a halide, an acetate, an oxalate, a citrate, a nitrate or an oxide of the above-described metals in aqueous or alcoholic solution.

Both ion exchange and impregnation can be followed by drying, optionally another calcination. In the case of metal-doped zeolites of the MCM-49 or MCM-56 type an aftertreatment with hydrogen and/or with steam may be beneficial.

A further modification option consists in the zeolites of the MCM-49 or MCM-56 type according to the invention—molded or not molded—being subjected to a treatment with acids such as hydrochloric acid (HCl), hydrofluoric acid (HF), sulfuric acid ($H_2SO_4$), phosphoric acid ($H_3PO_4$), oxalic acid ($HO_2C—CO_2H$) or mixtures thereof.

A particular embodiment comprises the zeolites of the MCM-49 or MCM-56 type according to the invention being treated, prior to molding, with one of said acids, from 0.001N to 2N, preferably from 0.05N to 0.5N, for from 1 to 100 hours under reflux. After filtration and washing, drying takes place as a rule at from 100° to 160° C. and calcination at from 200° to 600° C. A further particular embodiment involves an acid treatment of the zeolites of the MCM-49 or MCM-56 type according to the invention after having been molded with a binder. In the process, the zeolite according to the invention is treated, as a rule, for from 1 to 3 hours at from 60° to 80° C. with a from 3 to 25% strength, in particular a from 12 to 20% strength acid, then washed, dried at from 100° to 160° C. and calcined at from 200° to 600° C. Here, again, calcination can take place directly in the amination reactor.

Another modification option is that of an exchange with ammonium salts, eg. with $NH_4Cl$ or with mono-, di- or polyamines. This involves the zeolite, molded together with binder, being exchanged, as a rule, at from 60° to 80° C. with from 10 to 25% strength, preferably 20% strength $NH_4Cl$ solution continuously for 2 h in a zeolite/ammonium chloride solution of 1:15 by weight and then being dried at from 100 ° to 120° C.

A further modification to which the zeolites according to the invention can be subjected is that of dealumination in the case of aluminum zeolites, in which some of the aluminum atoms are replaced by silicon or the zeolites are depleted, in terms of their aluminum content, by hydrothermal treatment, for example. A hydrothermal dealumination is advantageously followed by an extraction with acids or complexing agents, to remove any non-lattice aluminum formed. The replacement of aluminum by silicon can take place, for example, with the aid of $(NH_4)_2SiF_6$ or $SiCl_4$. Examples of dealuminations of Y-zeolites can be found in Corma et al., Stud. Surf. Sci. Catal. 37 (1987), pp. 495 to 503. In the case of other trivalent oxides the modulus can be increased correspondingly by a fraction of the boron, the iron or the gallium being leached out or being replaced by silicon.

The catalysts can be employed for the amination of the olefins as extrudates having diameters of eg. from 1 to 4 mm or as pellets having a diameter of eg. from 3 to 5 mm.

The catalyst, for example molded into extrudates, can be converted, by grinding and screening, into a fluidizable material having a size of from 0.1 to 0.8 mm.

The substituents $R^1$, $R^2$, $R^3$, $R^4$, $R^5$ and $R^6$ in the compounds I, II and III have the following meanings:

$R^1$, $R^2$, $R^3$, $R^4$, $R^5$, $R^6$ hydrogen, $C_1$- to $C_{20}$-alkyl, preferably $C_1$- to $C_{12}$-alkyl, particularly preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$- to $C_{20}$-alkenyl, preferably $C_2$- to $C_{12}$-alkenyl, particulary preferably $C_2$- to $C_8$-alkenyl such as vinyl and allyl, $C_2$- to $C_{20}$-alkynyl, preferably $C_2$- to $C_8$-alkynyl, in particulary $C_2H$ and propargyl, $C_3$- to $C_{20}$-cycloalkyl, preferably $C_3$- to $C_{12}$-cycloalkyl, particularly preferably $C_5$- to $C_8$-cycloalkyl such as cyclopentyl, cyclohexyl, cycloheptyl and cyclooctyl, $C_4$- to $C_{20}$-alkyl-cycloalkyl, preferably $C_4$- to $C_{12}$-alkyl-cycloalkyl, particularly preferably $C_5$- to $C_{10}$-alkyl-cycloalkyl, $C_4$- to $C_{20}$-cycloalkyl-alkyl, preferably $C_4$- to $C_{12}$-cyclo-alkyl-alkyl, particularly preferably $C_5$- to $C_{10}$-cycloalkylalkyl, aryl such as phenyl, 1-naphthyl and 2-naphthyl, preferably phenyl, $C_7$- to $C_{20}$-alkylaryl, preferably $C_7$- to $C_{16}$-alkylaryl, particularly preferably $C_7$- to $C_{12}$-alkylphenyl such as 2-methylphenyl, 3-methylphenyl, 4-methylphenyl, 2-ethylphenyl, 3ethylphenyl and 4-ethylphenyl, $C_7$- to $C_{20}$-aralkyl, preferably $C_7$- to $C_{16}$-aralkyl, particularly preferably $C_7$- to $C_{12}$-phenalkyl such as phenylmethyl, 1-phenylethyl, 2-phenylethyl, $R^1$ and $R^2$ jointly a saturated or unsaturated $C_3$- to $C_9$-alkylene divalent chain, preferably—$(CH_2)_4$—, —$(CH_2)_5$—, —$(CH_2)_7$— and —CH=CH—CH=CH—, $R^3$ or $R^5$ $C_{21}$- to $C_{200}$-alkyl, preferably $C_{40}$- to $C_{200}$-alkyl, such as polybutyl, polyisobutyl, polypropyl, polyisopropyl and polyethyl, particularly preferably polybutyl and polyisobutyl, $C_{21}$- to $C_{200}$-alkenyl, preferably $C_{40}$- to $C_{200}$-alkenyl, particularly preferably $C_{70}$- to $C_{170}$-alkenyl, $R^3$ and $R^5$ jointly a $C_2$- to $C_{12}$-alkylene divalent chain, preferably a $C_3$- to $C_8$-alkylene divalent chain, particularly preferably —$(CH_2)_3$—, —$(CH_2)_4$—, —$(CH_2)_5$—, —$(CH_2)_6$— and —$(CH_2)_7$—, in particulary —$(CH_2)_3$— and —$(CH_2)_4$—.

EXAMPLES

Catalyst syntheses

Catalyst A: Na-MCM-49

20.2 g of sodium aluminate were added to 10 g of NaOH in 870 g of water, and 171 g of Aerosil 50® (from Degussa) were added. The mixture was stirred briefly until it appeared to be homogeneous, followed by the addition of 90 g of hexamethylene imine. The mixture was then transferred into an autoclave and crystallized at 150° C. for 84 h under intrinsic pressure with stirring. The zeolite formed was filtered off and washed, dried for 4 h at 110° C. and calcined for 16 h at 550° C. It had a modulus of 29. The analysis of the diffractogram in the uncalcined state indicated the formation of MCM-49.

Catalyst B: H-MCM-49

150 g of catalyst A were stirred with 2250 g of a 20% strength $NH_4Cl$ solution for 2 h at 80° C. and then filtered off and washed with 4 of water. After renewed $NH_4Cl$ exchange and rewashing with 12 of water, the zeolite was dried for 2 h at 120° C. and calcined for 5 h at 500 ° C. The entire procedure was then repeated once more. The sodium analysis gave a value of 0.07%.

60 g of exchanged zeolite were compacted in a kneader with 40 g of boehmite and 2 g of formic acid and were kneaded for 30 min with the addition of water (96 ml). An extruder was used, with an extrusion pressure of 70 bar, to produce 2 mm extrudates which were dried for 4 h at 120° C. and calcined for 16 h at 500° C.

Catalyst C: Na-MCM-49

15 g of sodium aluminate were added to 10 g of NaOH in 870 g of water, and 171 g of Aerosil 50® (from Degussa) were added. The mixture was stirred briefly until it appeared to be homogeneous, followed by the addition of 90 g of hexamethylene imine. The mixture was then transferred into an autoclave and crystallized at 150° C. for 84 h under intrinsic pressure with stirring. The zeolite formed was filtered off and washed, dried for 4 h at 110° C. and calcined for 16 h at 550° C. It had a modulus of 39. The analysis of the diffractogram in the uncalcined state indicated the formation of MCM-49.

Catalyst D: H-MCM-49

100 g of catalyst C were stirred with 1500 g of a 20% strength $NH_4Cl$ solution for 2 h at 80° C. and then filtered off and washed with 5 of water. After renewed $NH_4Cl$ exchange and rewashing with 10 of water, the zeolite was dried for 2 h at 120° C. and calcined for 5 h at 500° C. The entire procedure was then repeated once more. 60 g of the exchanged zeolite were compacted in a kneader with 40 g of boehmite and 2 g of formic acid and were kneaded for 35 min with the addition of water (100 ml). An extruder was used, with an extrusion pressure of 55 bar, to produce 2 mm extrudates which were dried for 16 h at 120° C. and calcined for 16 h at 500° C.

Catalyst E: Na-MCM-49

25 g of sodium aluminate were added to 10 g of NaOH in 870 g of water, and 171 g of Aerosil 50® (from Degussa) were added. The mixture was stirred briefly until it appeared to be homogeneous, followed by the addition of 90 g of hexamethylene imine. The mixture was then transferred into an autoclave and crystallized at 150° C. for 84 h under intrinsic pressure with stirring. The zeolite formed was filtered off and washed, dried for 4 h at 110° C. and calcined for 5 h at 500° C. It had a modulus of 23. The analysis of the diffractogram in the uncalcined state indicated the formation of MCM-49.

Catalyst F: H-MCM-49

100 g of catalyst E were stirred with 1500 g of a 20% strength $NH_4C$ solution for 2 h at 80° C. and then filtered off and washed with 5 of water. After renewed NH₄Cl exchange and rewashing with 10 of water the zeolite was dried for 2 h at 120° C. and calcined for 5 h at 500° C. The entire procedure was then repeated once more.

80 g of the exchanged zeolite were compacted in a kneader with 53 g of boehmite and 3 g of formic acid and were kneaded for 60 min with the addition of water (110 ml). An extruder was used, with an extrusion pressure of 50 bar, to produce 2 mm extrudates which were dried for 4 h at 120° C. and calcined for 16 h at 500° C. The sodium analysis gave a value of 0.11%. ps Amination examples The experiments were carried out in a tubular reactor (internal diameter 6 mm) under isothermal conditions at from 260° to 300° C. and at 280 bar, using a mixture of isobutene and ammonia in a molar ratio of 1:1.5. The reaction products were analyzed in a gas chromatograph.

The results are summarized in Table 1.

TABLE 1

| Catalyst | Temperature [°C.] | Yield of t-butylamine [wt %] | | | Weight per liter [kg/l] |
| --- | --- | --- | --- | --- | --- |
| | | WHSV 0.75 [g/g · h] | WHSV 1.5 [g/g · h] | WHSV 3 [g/g · h] | |
| B | 260 | 21.72 | | | 0.45 |
| B | 270 | | 19.26 | 15.73 | 0.45 |
| B | 280 | | 18.80 | 17.66 | 0.45 |
| B | 300 | | | 13.36 | 0.45 |
| D | 260 | 17.08 | | | 0.45 |
| D | 270 | 20.83 | 15.99 | 11.22 | 0.45 |
| D | 280 | 19.06 | 17.74 | 14.90 | 0.45 |
| D | 300 | | | 13.17 | 0.45 |
| F | 260 | 18.33 | | | 0.41 |
| F | 270 | 20.91 | 17.04 | 12.36 | 0.41 |
| F | 280 | 19.37 | 18.33 | 15.51 | 0.41 |
| F | 300 | | | 13.48 | 0.41 |

We claim:

1. A process for preparing amines of the formula I

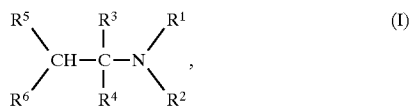

where $R^1, R^2, R^3, R^4, R^5, R^6$ are hydrogen, $C_1$- to $C_{20}$-alkyl, $C_2$- to $C_{20}$-alkenyl, $C_2$- to $C_{20}$-alkynyl, $C_3$- to $C_{20}$-cycloalknyl, $C_4$- to $C_{20}$-alkyl-cycloalkyl, $C_4$- to $C_{20}$-cycloalkyl-alkyl, aryl, $C_7$- to $C_{20}$-alkylaryl or $C_7$- to $C_{20}$-aralkyl, $R^1$ and $R^2$ jointly are a saturated or unsaturated $C_3$- to $C_9$-alkylene divalent chain and $R^3$ or $R^5$ are $C_{21}$- to $C_{200}$-alkyl, $C_{21}$- to $C_{200}$-alkenyl or jointly are a $C_2$- to $C_{12}$-alkylene divalent chain, by reacting olefins of the formula II

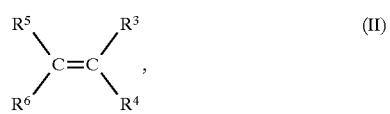

where $R^3$, $R^4$, $R^5$ and $R^6$ have the abovementioned meanings, with ammonia or primary or secondary amines of the formula III

where $R^1$ and $R^2$ have the abovementioned meanings, at from 200° to 350° C. and from 100 to 300 bar in the presence of a heterogeneous catalyst, wherein the heterogeneous catalyst used comprises zeolites of the MCM-49 or MCM-56 type.

2. A process for preparing amines I as defined in claim 1, wherein the amine I formed is separated off and the unreacted starting materials II and III are recycled.

3. A process for preparing amines as defined in claim 1, wherein the olefin II used is isobutene, diisobutene, cyclopentene, cyclohexene or polyisobutene.

4. A process for preparing amines as defined in claim 1, wherein the heterogeneous catalysts used comprise zeolites of the MCM-49 or MCM-56 type in the H form.

5. A process for preparing amines as defined in claim 1, wherein the heterogeneous catalysts used comprise zeolites of the MCM-49 or MCM-56 type which have been treated with an acid from the group consisting of hydrochloric acid, hydrofluoric acid, sulfuric acid, phosphoric acid, oxalic acid or mixtures thereof.

6. A process for preparing amines as defined in claim 1, wherein the heterogeneous catalysts used comprise zeolites of the MCM-49 or MCM-56 type which are doped with one or more transition metals.

7. A process for preparing amines as defined in claim 1, wherein the heterogeneous catalysts used comprise zeolites of the MCM-49 or MCM-56 type which are doped with one or more rare earth elements.

8. A process for preparing amines as defined in claim 1, wherein the heterogeneous catalysts used comprise zeolites of the MCM-49 or MCM-56 type in the ammonium form.

9. A process for preparing amines as defined in claim 1, wherein the heterogeneous catalysts used comprise zeolites of the MCM-49 or MCM-56 type which are doped with one or more elements from the group consisting of the alkali metals, alkaline earth metals or earth metals.

10. A process for preparing amines as defined in claim 1, wherein the heterogeneous catalysts used comprise zeolites of the MCM-49 or MCM-56 type which have been molded with a binder and calcined at from 200° to 600° C.

11. A process for preparing amines as defined in claim 1, wherein the heterogeneous catalysts used comprise dealuminated or deboronated zeolites of the MCM-49 or MCM-56 type.

12. A process for preparing amines as claimed in claim 1, wherein the heterogeneous catalysts used comprise [Al]-MCM-49 zeolites.

* * * * *

UNITED STATES PATENT AND TRADEMARK OFFICE
CERTIFICATE OF CORRECTION

PATENT NO.: 5,840,988

DATED: November 24, 1998

INVENTOR(S): ELLER et al.

It is certified that error appears in the above-identified patent and that said Letters Patent is hereby corrected as shown below:

Col. 7, claim 1, line 47, "cycloalkynyl" should be --cycloalkyl--.

Signed and Sealed this

Thirtieth Day of March, 1999

Attest:

Q. TODD DICKINSON

*Attesting Officer*    *Acting Commissioner of Patents and Trademarks*